United States Patent [19]

Schuhmann

[11] Patent Number: 4,893,625
[45] Date of Patent: Jan. 16, 1990

[54] INSERTION TYPE ELECTRODE ARRANGEMENT FOR CONTINUOUS $PO_2$ MEASUREMENT IN LIVING SKIN TISSUE

[76] Inventor: Rolf Schuhmann, Grosser Hasenpfad 25, D-6000 Frankfurt am Main 70, Fed. Rep. of Germany

[21] Appl. No.: 20,942
[22] PCT Filed: May 17, 1986
[86] PCT No.: PCT/DE86/00210
§ 371 Date: Jan. 20, 1987
§ 102(e) Date: Jan. 20, 1987
[87] PCT Pub. No.: WO86/06945
PCT Pub. Date: Dec. 4, 1986

[30] Foreign Application Priority Data

May 23, 1985 [DE] Fed. Rep. of Germany ....... 3518463

[51] Int. Cl.[4] ............................................. A61B 5/00
[52] U.S. Cl. .................................... 128/635; 128/642; 204/403; 204/431
[58] Field of Search ................ 128/635, 642; 204/403, 204/431

[56] References Cited

U.S. PATENT DOCUMENTS

| | | | |
|---|---|---|---|
| 3,415,730 | 12/1968 | Haddad | 204/403 |
| 3,476,670 | 11/1969 | Weiner | 128/635 X |
| 4,294,258 | 10/1981 | Bernard | 128/635 |
| 4,320,764 | 3/1982 | Hon | 128/635 |
| 4,582,064 | 4/1986 | Sorger | 128/635 |

FOREIGN PATENT DOCUMENTS

2930663 2/1981 Fed. Rep. of Germany .
2120787 8/1972 France .

OTHER PUBLICATIONS

Neuman et al, "Application of Oxygen Cathodes ... ", 24th ACEMB-Las Vegas, Nev., Oct. 31–Nov. 4, 1971, p. 249.
Kopernik, "Die Ableitung ... Skalpelektrode", Dtsch Gesundheitsu, 26: 1756-8, 9 Sep. 71.
Aarnoudse et al, "Fetal Subcutaneous Scalp $pO_2$ ... ", Am J ob Gyn, vol. 53, No. 5, Nov. 1, 1985, pp. 565-566.

*Primary Examiner*—Lee S. Cohen
*Attorney, Agent, or Firm*—Toren, McGeady & Associates

[57] ABSTRACT

It is possible by means of a new spiral electrode arrangement to measure the $pO_2$ partial pressure of restless moving tissue, for example on a child during labor. At the same time the electrode arrangement allows measurement of the child's heartbeat frequency pattern during labor. By graphically representing both measurement patterns a doctor can determine when he must, for example, accelerate the birth or initiate other clinical measures.

13 Claims, 4 Drawing Sheets

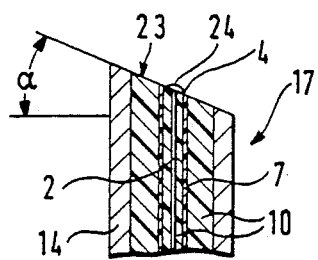
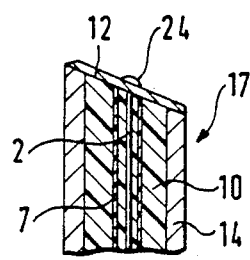
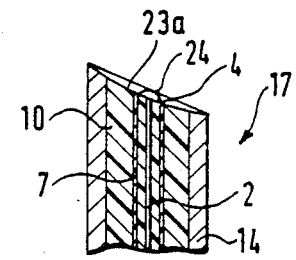
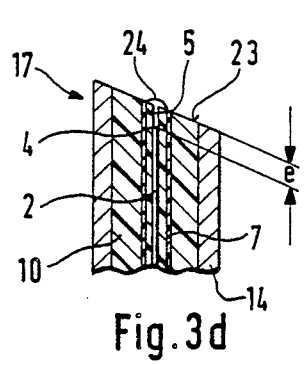
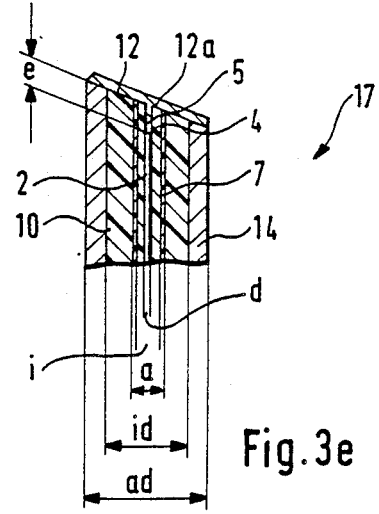
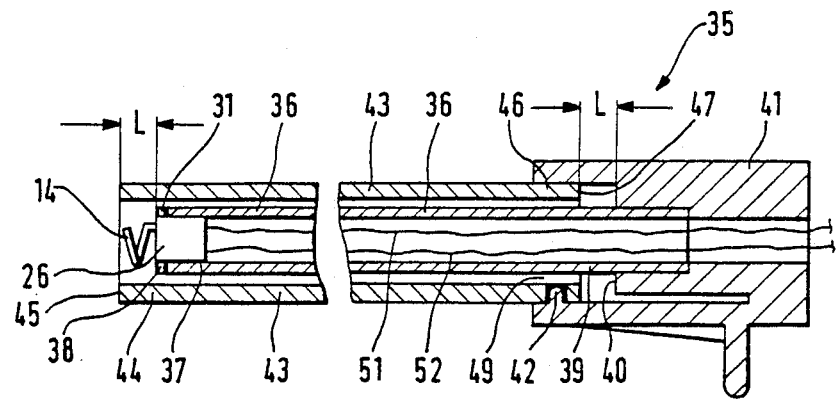

INSERTION TYPE ELECTRODE ARRANGEMENT FOR CONTINUOUS PO2 MEASUREMENT IN LIVING SKIN TISSUE

The present invention is directed to an insertion type electrode arrangement for continuous $pO_2$ measurement in living skin tissue with an outer metal tube electrode and an electrically insulated platinum wire electrode arranged therein.

A process and an electrode arrangement for transcutaneous $pO_2$ measurement has been developed by Lubbers and Huch (1960). While this process has shown good results in the intensive care of newborn, its application for instance in the province of birth assistance is problematical: For one the arrangement of the electrodes (external diameter 18 mm) provided by Lubbers and Huch is not simple, besides these electrodes are heated to 44° C., so that indeed the "arterial" oxygen partial pressure can be measured, but on the other hand the heating process could cause changes in the skin after approximately 3 hours, with the consequence that the electrode has to be applied at another point.

A $pCO_2$ electrode arrangement (Lubbers, Huch, 1980) also measures according to the transcutaneous process; the same applies for this measuring system as it did for the transcutaneous $pO_2$ electrode arrangement.

The measurement of the oxygen partial pressure is based on the polarization phenomenon, meaning oxygen molecules which reach a platinum cathode generate an electric current which is proportional to the quantity of the oxygen molecules. The electrode is connected to a polarization voltage of for instance 750 mV and is constructed in such a way, that the oxygen from the blood or the tissue diffuses through a thin, electrically insulating, but gas-permeable membrane towards the platinum cathode. The current (polarization current) flowing through the electrode is measured by an ammeter. Said current is proportional to the oxygen partial pressure in the tissue at the electrode tip. Since, however, there exists no absolute reaction between the polarization current and the $pO_2$ existing at the electrode tip, each oxygen electrode must be calibrated with calibration gases whose $pO_2$ is known (0.9% NaCL solution with the known oxygen content—20%, 10%, 0% -0.9% -NaCl solution with nitrogen proportionally equilibrated]).

The general reaction is :

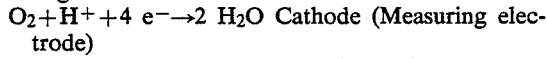
$O_2 + H^+ + 4\ e^- \rightarrow 2\ H_2O$ Cathode (Measuring electrode)

$4\ Ag + 4\ CL^- \rightarrow 4\ AgCL + 4\ e^-$ (Anode)

Overall Reaction

$O_2 + 4\ Ag + 4\ H^+ + 4\ CL^- \rightarrow 4\ AgCL + 2\ H_2O$

In the year 1956 Clark introduced a platinum electrode for measurement of the oxygen partial pressure. Since this time a series of $pO_2$ electrode arrangements have been developed in accordance with Clark. Micro- and macroelectrodes as straight puncture eletrodes for $pO_2$ measurement in human tissue have been increasingly used in surgery, internal medicine and pharmacology (First Symposium of Tissue Oxygen Pressure Measurement 1982, Second Tissue Oxygen Pressure Symposium 1983 in Frankfurt "Determination of Tissue Oxygen Pressure in Patient",Professor A. M. Ehrly, Pergamon-Press).

Puncture electrodes in straight form for $pO_2$ measurement have been successful where the tissue of the patient or the child to be examined is relatively quiescent.

An insertion type electrode for continuous $pO_2$ measurement in living skin tissue has for instance become known, consisting of a cathode, which is fused gas tight into the glass capillary and fixed in a hollow member, wherein the hollow member is connected in such a way through a grid with a shielding of the coaxial cable, that the grid completely surrounds the resin embedding, the connecting point, of the cathode with the copper core of the coaxial cable, said grid enclosing the connecting point on all sides, and in which a tube consisting preferably of silver is ground-in in cannula fashion and which exhibits a thickening at the other end, wherein a hook is rigidly connected with the tube and exhibits a contact face at the lower side of the electrode member, which has a recess on both sides beneath the front cavity of the hook (DD 88 835).

The particularity of this known insertion type electrode for continuous partial oxygen pressure measurement in living skin tissue is to be seen therein, that the external metal tube electrode serving as anode consists of silver/silver oxide and serves as a reference electrode. The electrically insulated platinum wire electrode arranged therein serves as the measuring electrode proper with a diameter of approximately 50 μm.

With such an electrode arrangement exact measurements can be performed in quiescent tissue. The insertion type electrode arrangement is equipped with a hook for fixing, which during the use is fastened with a surgical clamp.

This electrode arrangement can, however, not be used where he partial oxygen pressure measurements must be performed on a moving patient preferably on a child at birth.

Therefore, the present invention is based upon the task to create an insertion electrode arrangement for measuring the oxygen partial pressure at restless and moving tissues, with which simultaneously other measurements can also be performed independently of the measurement of the oxygen partial pressure.

In the invention this task is solved by designing both the metal electrodes in spiral shape and seating one of their terminal ends in a cylindrical plastic member, from which they are connectible to different measuring apparatus and reference electrodes independent of each other.

It is thus possible to perform continuous oxygen partial pressure measurements during labor. The electrode arrangement is simply inserted into the skin tissue of the child and indeed into the forward pointing part of the tissue. The electrode arrangement is seated so strongly in the tissue, as tests have shown, that the oxygen partial pressure measuring values and the heartbeat frequency measuring values are reliably available during the entire birth process. Ag/Ag-CL electrodes are fixed independently of each other at the skin surface of the mother by way of reference electrodes. With the help of the novel insertion electrode arrangement it is thus possible to measure the oxygen partial pressure as well as the heart frequency during labor. The measuring values determined independently of each other can be brought into relation with each other in such a way by electronic evaluation apparatus, so that the physician receives dependable statements concerning oxygen partial pressure and the heartbeat frequency of the child during labor.

The measurement of these two very important parameters with only one insertion electrode arrangement was hitherto not possible.

Spiral electrodes are indeed known for being fixed in the tissue, (EP 0 104 619, U.S. Pat. No. 4, 320, 764), however these are not suited for the solution of the task of the invention. The EP No. 0 104 619 is directed to the combination of a spiral electrocardiogram electrode with a device for measurement of the pH-value. Photoconductors are used for this, which are slid into a spiral hollow needle. The ends of the photoconductors leading out of the spiral protective tube are connected to a light source or to a light sensor.

The diameter of the spiral protective tube electrode is so large that both photoconductors can be placed therein without difficulty. The photoconductors need not be insulated against each other and also not against the metallic protective tube electrode.

The measurement of the pH-value is under certain circumstances important, it can however not replace the measurement of the oxygen partial pressure. The known electrode arrangement with photoconductor could not supply a stimulus to design two metallic electrodes which are electrically insulated against each other, one inside the other in a spiral shape and to connect each of the metallic electrodes with a measuring apparatus with its own reference electrodes, so that independently of each other under labor conditions two important measuring sequences, namely, concerning the $pO_2$ pressure and the heart frequency are obtainable.

The U.S. Pat. No. 4,320,764 is directed to a spiral electrode, which is seated with its terminal end in a plastics body. A metal electrode is attached at the end of the plastic body lying opposite to the spiral electrode. An electrical potential is generated between the two electrodes as a consequence of their chemical properties and of the liquor amnii, which supplies information about the respective pH-values of the fetus.

A simultaneous measurement of two important measuring sequences as with the insertion type electrode arrangement according to the invention is impossible.

In order to enable a secure insulation between the metal electrodes, the platinum wire electrodes within the metal tube electrode is surrounded by a cellophane sleeve. Thus it is essentially prevented that the insulation between the platinum wire electrode and the metal tube electrode is impaired already during the manufacturing process of the electrode arrangement.

In order to be absolutely sure the inside space of the metal tube electrode is filled with synthetic resin, araldite XW 39 Ciba-Geigy, Federal Republic of Germany, preferably with application of vacuum.

It is of particular importance that the metal tube electrode with the terminal end of the platinum wire electrode is seated eccentrically in the edge area of the front face of the plastics body. It is thus achieved that the electrode arrangement designed as an open spiral can be placed in front of the front face of the plastics body, wherein the diameter of the spiral electrode arrangement is smaller than the diameter of the plastics body.

Two attachment pieces lying opposite each other are arranged in the contour of the plastics body, which project out of the contour surface. They serve in connection with an insertion assistance to insert the electrode arrangement preferably during labor into the tissue of the leading portion of the child.

In one embodiment example of the front end face of the electrode arrangement there is a ground-off face with an angle of inclination of approximately 20° with respect to the metal tube electrode. This facilitates the insertion of the electrode arrangement into the tissue of the skin. Therein the measuring face of the platinum wire electrode can impinge flush upon the tissue. Hereby a small $pO_2$ depletion zone arises above the measuring face (platinum), which is indeed very small measuring technology-wise, however it does not assure stable conditions. Because of this such a measuring electrode has indeed a high response sensitivity, however it is extraordinarily sensitive to motion or sensitive to stirring. Such electrode arrangement can however always be used advantageously where essentially only the response sensitivity is important. Exact measuring values are hardly supplied or only then if disturbance frequencies are electronically blended out.

An improvement in the measuring results can be achieved if the ground-off face and the measuring face are covered by an electrically insulating gas-permeable membrane. Depending upon the thickness of this membrane the oxygen partial pressure depletion zone becomes more flat, meaning the response sensitivity as well as the stirring effect decrease. It is possible to adjust or regulate the corresponding values through the thickness of the membrane In the present case, however, the covering of the ground-off face with the membrane is difficult, because the front region at the electrode arrangement is composed starting from the outside of a metal ($V_2A$) jacket, a synthetic resin jacket, a cellophane jacket, a synthetic resin jacket lying therein and the platinum wire measuring electrode. "Unsticking phenonema" of the membrane can occur during use of the electrode arrangement in liquid with the consequence that the electrode arrangement must be newly recovered after each use. Because of the new covering a change of the measuring values occurs so that the electrode arrangement had to be newly calibrated. Tests have shown that the reduction of the depletion zone in front of the measuring face can be achieved by a so-called recessing distance, through which the measuring face of the measuring electrode is set back behind the ground-off face.

Particularly good results are achieved with electrode arrangements whose front region exhibits a recessed distance, which is covered by a membrane, whose rearward portion fills the recessed distance. Through this a defined thickness of the membrane is achieved. To this it must be added that the membrane adheres better at the synthetic resin wall within the protective tube and thus does not tend to unstick phenomena.

During experiments with animals electrodes of this construction remained in part over 48 hours in the tissue, without that drifts or changes could be observed in the measuring values. The calibration curve prior to the experiment varied compared to the that after the experiment by less than 5%. Such an embodiment of the front areas of electrode arrangement is not limited to spiral curvature of this electrode arrangement. The novel coating with the membrane can be utilized in all appropriate measuring electrode arrangements.

A process for manufacture of such an electrode arrangement, consisting of a platinum wire electrode and a metal tube electrode electrically insulated from and surrounding said platinum wire electrode, said metal tube electrode being preferably from $V_2A$-steel with a recessed distance in the front region, is essentially characterized in that the front region of the platinum wire electrode is electrolytically decomposed.

In detail this decomposition occurs in that the front region of the electrode arrangement is dipped into a salt solution, in which is located a small platinum plate, whereupon the platinum wire electrode is connected to the negative terminal and the small platinum plate to the positive terminal of a direct current source for the duration of an adjustable time period corresponding to the desired length of the recess distance and that subsequently a thorough cleaning of the front region of the electrode arrangement occurs.

After the cleaning the coating of the front region of the electrode arrangement with the membrane and the filling of the recessed distance with the material of the membrane is performed in vacuum conditions.

BRIEF DESCRIPTION OF THE DRAWINGS

An embodiment example of the invention is described with particularity in the following with the help of the It is shown on:

FIGS. 3a-3e section through various embodiment forms of the front region of the electrode arrangement, FIG. 4 a section through the insertion assistance with the electrode arrangement, FIG. 5 a schematic illustration of the application of the electrode arrangement to the leading portion of a child under labor conditions, FIGS. 6a-6c a greatly simplified illustration of the oxygen partial pressure distribution in the upper region of the skin, a graph and a schematic illustration of the functional mode of an application of the invention and FIG. 7 a schematic illustration of the use of the

DETAILED DESCRIPTION OF THE DRAWINGS

Figure 1:
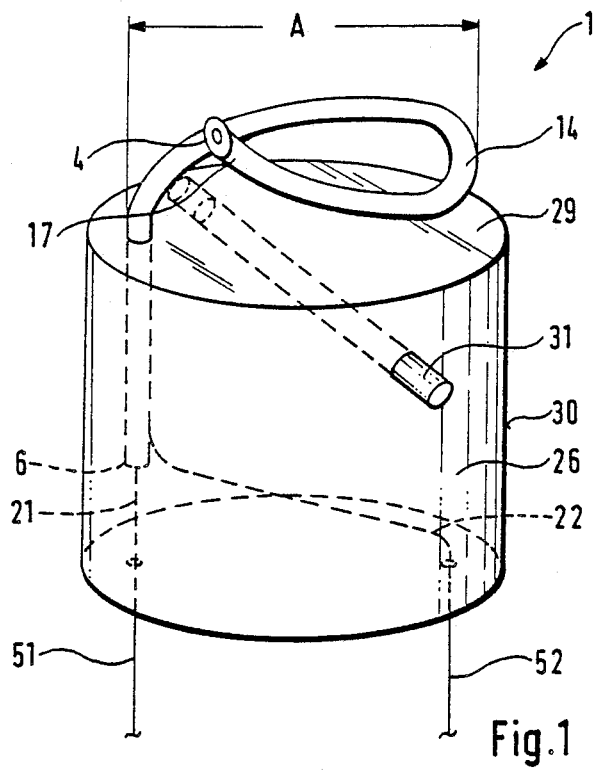
FIG. 1 a magnified front view of the electrode arrangement in perspective.

FIG. 1 shows the view of an electrode arrangement 1 in perspective with two spirally designed metal electrodes 2, 14, which essentially consists of a metal tube electrode 14 and an electrically insulated platinum wire electrode 2 arranged therein as well as a cylindrical plastics body 26 which in a preferred embodiment example is manufactured from araldite XW 39 (of the Ciba-Geigy Corp.).

Figure 2:
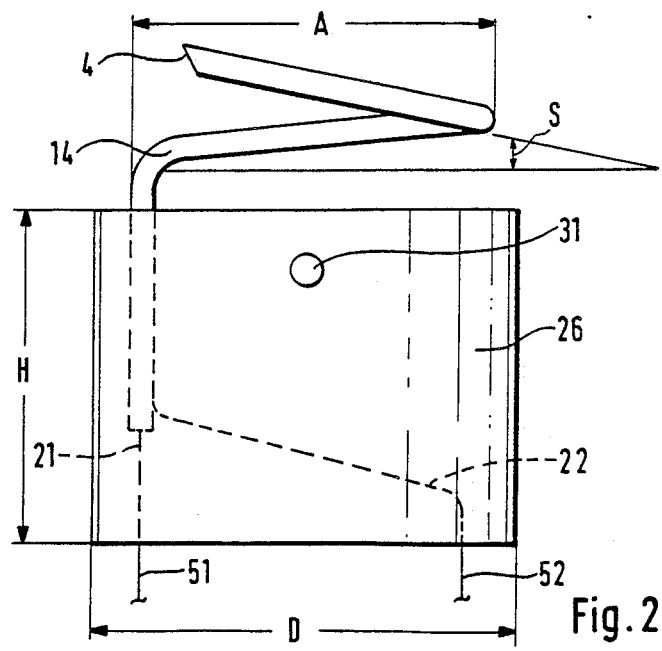
FIG. 2 a side view of the electrode arrangement according to FIG. 1.
Figure 5:
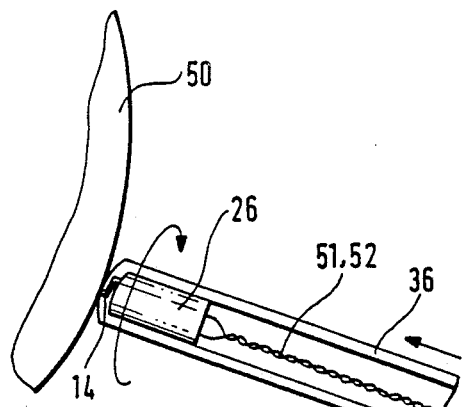

According to FIG. 2 the height of said plastics body is designated with H and its diameter with D. In a preferred embodiment example the height amounts to 5 mm and the diameter to 4.5 mm.

The metal tube electrode 14 protrudes eccentrically from one of the front faces 29 of the plastics body 26 meaning it protrudes from its edge area, the platinum wire electrode 2 being arranged in said metal tube electrode. The metal tube electrode 14 is designed as a so-called open spiral with a slope S (FIG. 2) of approximately 30°. The platinum wire electrode 2 exhibits a front measuring face 4, which as will be explained in detail later, is designed as a portion of an outwardly pointing ground-off face 23, 23a with an angle of inclination $\alpha$ of approximately 20° with respect to the metal tube electrode 14.

Figure 7:
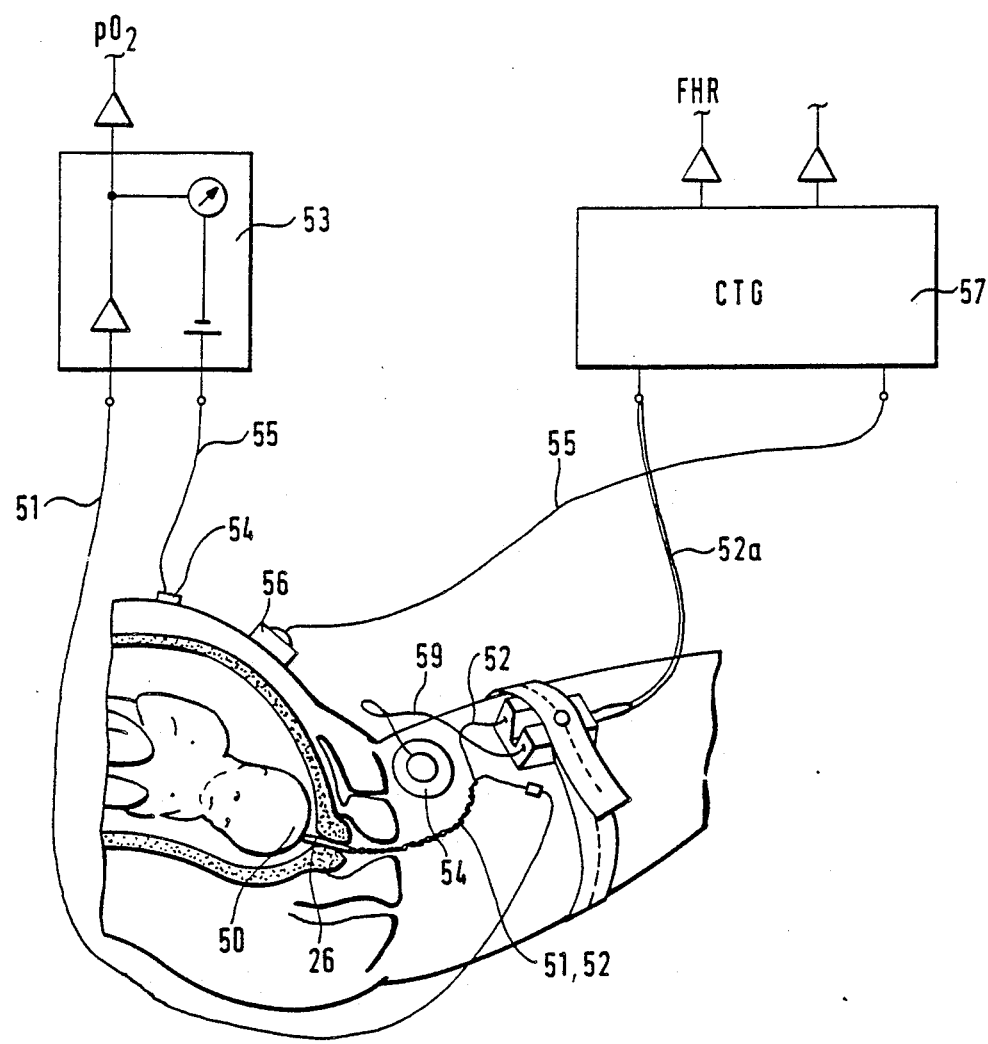

The platinum wire electrode 2 designed as pO$_2$-sensor has a terminal end 6, which is connected by a connecting line 21 to a line 51 which according to FIG. 7 is in connection with a pO$_2$ measuring apparatus 53

As can principally be recognized from the FIG. 3a-3, the platinum wire electrode 2 sits electrically insulated in the metal tube electrode 14. The platinum wire electrode 2 is embraced by a cellophane sleeve 7 within the metal tube electrode 14. Additionally the inside space of the metal tube electrode 14 is filled with synthetic resin 10. In order to achieve a very secure insulation of the metal tube electrode against the platinum wire electrode, the synthetic resin 10 is preferably introduced into the inside space of the spiral metal tube electrode 14 with the use of vacuum.

In detail the platinum wire electrode 2 serves as a pO$_2$-sensor and has a diameter d of approximately 20 $\mu$m. It is threaded into the cellophane sleeve 7, which on its part exhibits an outside diameter 1 of approximately 200 $\mu$m and an inside diameter i of approximately 180 $\mu$m. The metal tube electrode 14 which in preferred embodiment examples consists of V$_2$A-steel, has an external diameter ad of approximately 450 $\mu$m and an internal diameter id of approximately 300 $\mu$m whose dimensions assure on the one hand good handling characteristics of the electrode arrangement and over and above that a comparatively simple manufacture.

From the jacket 30 of the plastics body 26 protrude two attachment pins 31 lying opposite each other and removed approximately 1 mm from the front face 29, whose significance will be explained later.

It can be discerned from FIG. 1 that a connecting line 22 is connected to the metal wire electrode 14 so as to be electrically conducting, which leads to a line 52 (FIG. 7), which in the illustrated embodiment example is connected by a connecting cable 52a through a terminal block, which connecting cable on its part is in switching connection with an additional measuring apparatus CTG or CardioTocoGraphy, i.e. an apparatus for recording the heartbeat/contractions during childbirth, by means of which during labor a peripheral cardial action potential for computation or determination of the heart frequency is derived.

Principally in FIG. 1 it can be clearly discerned that the metal tube electrode 14 with the enclosed platinum wire electrode 2 constitutes a (partial-) spiral winding with a slope S of approximately 30°, whose external diameter A is smaller than the diameter D of the plastics body 26.

An embodiment example of the electrode arrangement 1 can be manufactured as follows:

I. Plastics Body 26

To start off with a disk with a thickness of 3 mm is cut off from a cast synthetic resin rod from araldite XW 39 C with an external diameter D of 4.5 mm. A hole with a diameter of 0.5 mm for the terminal end 6 of metal tube electrode 14 and for the connecting line 21 is drilled proceeding from the planar section and spaced approximately 0.5 mm from the contour surface 30. In addition a hole with a diameter of 0.3 mm for receiving the fastening pin 31 is drilled transversely through the synthetic resin rod 2 mm from the planar section.

II. Platinum Wire Electrode 2

A platinum wire of 0.02 mm diameter d and a length of 5 cm is threaded into a cellophane sleeve 7 of a 3 cm length with an external diameter a of 0.2 mm and an internal diameter i of 0.18 mm. For stabilization purposes a platinum wire with a thickness of 0.07 mm is additionally inserted into the one end of the cellophane sleeve 7. Said wire projects only approximately by 3 mm into the cellophane sleeve 7 and serves for stabilizing the 0.02 mm thick platinum wire during the later soldering process. Then the cellophane sleeve 7 is introduced into the still straight metal tube electrode 14, so that its end with the two platinum wires protrudes by 1 mm from the metal tube. Subsequently the metal tube is bent to an angle of approximately 30° 2 mm from the end from which the two platinum wires protrude and this bent off end is curved with rounded pliers (4 mm diameter) through 180°. Subsequently the metal tube electrode 14 containing the platinum wire electrode tube is immersed into liquid synthetic resin, and the container is exposed for 10 minutes to a vacuum of $10^{-4}$ Torr. In this way when the vacuum is removed it is assured that the synthetic resin fills all the cavities in the metal tube electrode 14. Then the coiled electrode arrangement 1 is dried for 24 hours. Subsequently the front region 17 of the metal tube electrode 14 and the platinum wire electrode 2 is ground and polished at an angle of 20° with wet emory paper (No. 400), whereby the ground-off face 23 is produced. By a special grinding process it is also possible to produce a lens-shaped offset ground-off face 23a.

The metal tube electrode 14 is now inserted into the upper side bore in the front face 29 of the plastics body 26 and cemented there. The two platinum wires project after that from the opposite end of the bore. This practice has shown that it is appropriate for the soldering operation to insert a small copper plate at a fixed point for the strand. For this purpose a copper sheet of 2 mm diameter (thickness 0.05 mm) is bonded to the electrode member opposite the bore with the two protruding platinum wires. The protruding ends of the two platinum wires are now soldered to the small copper plate. Subsequently the plastics body 26 is inserted into a polyvinylchloride hose (inside diameter 4.5 mm), so that the metal tube electrode 14 closes the polyvinylchloride hose with its end. The length of the polyvinylchloride hose is 5 mm. The copper soldering spot is now soldered with a copper strand of approximately 0.4 mm thickness. Synthetic resin is poured into the space between this soldered spot in the inside and the upper edge of the PVC hose. After a drying operation lasting 24 hours the PVC-hose is removed.

Now a steel pin is inserted through the transverse bore in the plastics body 26 and cemented to same, so that its 1 mm beyond the surface contour 30 and thus constitute the fastening pins 31.

In the simplest case the front region 17 of the metal tube electrode 14 with the measuring face 4 of the platinum wire electrode 2 is coated (immersed) with polystyrene (Plastics Handbook, Volume 1, Basic Concepts, page 936, Carl Hauser Edition) of different concentrations and is dried. This coating serves as a membrane 12 or 12a. Subsequently the electrode arrangement 1 is measured or calibrated in a $O_2$ equillibrated and $N_2$ saturated 0.9% NaCL solution.

III. Prior to introduction of the metal tube electrode 14 into the plastics body 26 a copper strand (external diameter 0.4 mm) is attached externally at its straight portion and is passed through the bore with the platinum wires and cemented in same. The ensuing sequence is as described above.

The FIGS. 3a–3e show different embodiment forms of the front region 17 of an electrode arrangement 1. Herein it is of no importance whether the metal tube electrode 14 is coiled or belongs to a so-called needle electrode. FIG. 3a shows a magnified cross-section through the front region 17 of electrode arrangement 1. The platinum wire electrode 2 is arranged within the metal tube electrode 14. Normally the metal tube electrode 14 consists of VA-steel.

The platinum wire electrode 2 ends in the measuring face 4 The cellophane sleeve 7 is indicated around the platinum wire electrode 2. The illustrations in the FIGS. 3a–3e are drawn at a magnified scale, wherein for reasons of better clarity the individual spacings and thickness of the components of the electrode arrangement 1 are not shown in their true proportions.

The metal tube electrode 14 and the cellophane sleeve 7 are filled with synthetic resin 10.

The end of the front region 17 of the electrode arrangement 1 exhibits a ground-off face 23, which is arranged inclined through an angle of inclination $\alpha$ of about 20° with respect to the longituninal wall of the protective tube 14.

In the front region 17 according to FIG. 3a a so-called small $pO_2$ depletion zone 24 is formed above the measuring face 4 during the operation, which is indeed very small from the measuring technology point of view, however it does not supply any stable measuring results. An electrode arrangement according to FIG. 3a exhibits indeed a high response sensitivity, on the other hand it is however very sensitive to motion, preferably sensitive to stirring. For direct exact measurement such electrodes are little suited. The measuring values are subject to large fluctuations and can solely lead to a sensible evaluation by average value calculation by computer or the like If, however, the ground-off face 23 is covered with a membrane 12 according to FIG. 3b, the $pO_2$ depletion zone becomes flatter depending on the thickness of the $pO_2$ permeable membrane. Because of this the response sensitivity and the stirring effect decrease. The corresponding values can be adjusted or regulated by the thickness of the membrane.

Nevertheless the front region 17 according to FIG. 3b has disadvantages, since the ground-off face is seen as very little homogeneous because of the material differences. The ground-off face exhibits, counted from the outside towards the inside, the metal annulus of the metal tube electrode 14, the annulus from synthetic resin 10, the annulus of the cellophane sleeve 7, an inner annulus from synthetic resin 10 and finally the measuring face 4 of the platinum wire electrode 2. The membranes utilized hitherto do not bond themselves sufficiently solidly simultaneously with all these materials. A good adhesion of the membrane in the area of the synthetic resin was assured up to now; in the area of the metal annulus of the metal tube electrode 14 there occur however defoliation phenomena during longer utilization in liquids. This entails that the electrode had to be newly coated after each use. In addition considerable changes of the measuring values occurred because of drift.

To be sure this disadvantage of an electrode arrangement according to FIG. 3b could be improved by designing the front region 17 according to FIG. 3c, in which the ground-off face 23a receded in lens-shaped manner behind a flat ground-off face 23, however there arose the wish to improve the design of an electrode arrangement according to FIG. 3.

A so-called recessed distance 5 with a length e is introduced for this purpose according to FIG. 3d. The recessed distance 5 is manufactured electrolytically. For this purpose at least the front region 17 of an electrode arrangement is dipped into a salt solution and the platinum wire electrode 2 is connected to the negative terminal of a direct current source and a platinum plate dipped into the salt solution is connected to a positive terminal of a direct current source. If now a direct current flows, the front region of the platinum wire electrode 2 is degraded electrolytically. The process is a function of the elapsed time and the voltage. In a special case a 3.5 mol KCL solution is utilized as a salt solution. The direct voltage amounts to 5 volt. If under these conditions a current of 30 milliamperes is allowed to flow for a time period of 10–40 seconds, the platinum of the platinum wire electrode 2 recedes by fractions of millimeters behind the ground-off face 23.

Through this alone the measuring current can be reduced by a half if this electrode arrangement is utilized rather than a bright electrode according to FIG. 3a. The motion sensitivity or stirring sensitivity also decreases noticeably with an electrode arrangement according to FIG. 3d.

In a preferred embodiment example the front region 17 of an electrode arrangement according to FIG. 3 is coated by a membrane 12, 12a. This coating occurs in a vacuum. The portion 12a of the membrane 12 fills herein the recessed distance 5. Thus a defined thickness of the membrane 12, 12a can be achieved. Additionally the membrane adheres better at the synthetic resin wall, so that defoliation phenomena of the membrane 12 do not occur. Electrode arrangements according to the construction in FIG. 3d remained during experiments with animals up to 48 hours in the tissue and have not caused any sort of drift or other changes of the measured values. Calibration curves of electrode arrangements according to FIG. 3e prior to and after the experiment varied by less than 5%.

As stated the electrode arrangements according to FIGS. 3d and 3e can be utilized in connection with needle electrodes as well as in connection with spiral electrode arrangements according to the present invention with equal success.

FIG. 4 shows a cross-section of the plastics body 26 and the metal tube electrode 14 together with an insertion assistance 35, which exhibits an inner tube 36, in whose insertion end 37 slots 38 have been provided, into which fit fastening pins 31 in the plastics body 26. The lines 51 and 52 pass through the inner tube 36 and they protrude out of its upper end.

The plastics body 26 is seated with such a loose fit in the insertion end 37 of the inner tube 36, that said inner tube can be pulled off the plastics body 26 without difficulty, when the metal tube electrode 14 has been inserted into the tissue 15 for instance into the skin of the head of a child.

The operator's end 39 of the inner tube 36 exhibits an edge, which as depicted in FIG. 4 is fitted into a locking cap 41 and is fastened in same.

An outer tube 43 is arranged around the inner tube 36 coaxially and displaceably in axial direction of the concentric tube, which is in actuating connection with the locking cap 41 in the position depicted in FIG. 4 by means of a snap-in device 42 and a snap-in opening 49. Herein a spacing L is provided between an edge 47 at the operator's end 46 of the outer tube 43 and bottom ring 40 in the locking cap 41. The same spacing L exists between the front face 29 of the plastics body 26 and the front edge 45 at the insertion edge 44 of the outer tube 43. If the snap-in device 42 is lifted up by means of a handle-like arrangement, the not-positioned snap-in nose of the snap-in device 42 lifts out of the snap-in opening 49 and the locking cap 41 can be pushed downwards by the distance 48 according to FIG. 4. Through this the inner tube 36 is slid forward to such an extent that merely the metal tube electrode 14 protrudes from the insertion end 44 of the tube 43.

In this position the open spiral of the metal tube electrode 14 can be inserted into the front portion or the tissue 15 of the skin of the head by a slight rotation under pressure. As soon as the open spiral is inserted into the skin of the head, the insertion assistance 35 can be pulled back, so that as can be discerned from FIG. 7, lines 51 and 52 can be connected either through the CTG-cable terminal block 58 or to the line 52. Mini plugs are provided for this purpose.

Single electrodes 54 and 56 from silver/silver chloride are connected by the electrode cables 55 to the pO-measuring apparatus 53 and to the CTG-measuring apparatus 57. An additional single electrode 54 can be connected to the measuring apparatus 57 by an additional electrode cable 59.

Apart from the respective oxygen partial pressure $pO_2$ in the tissue of the child a peripheral, cardiac action potential for determination of the heart frequency can be derived with the new electrode arrangement and with the measuring apparatus 53 and 57 explained in FIG. 7. Should this fall beneath a preset value and remain for a long time span at this lowered value, for instance the acceleration of the birth or other clinical measures must be initiated.

The funtional mode of the electrode arrangement according to the invention is explained with reference to FIGS. 6a, 6b and 6c.

Figure 6A:
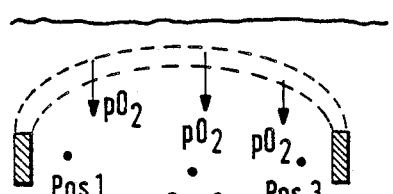

FIG. 6a shows in rough schematic fashion, that the arterial blood rich in oxygen flows through thin vessels to the venous thigh and herein in the path of the final flow, which consists only of a pure epithelium layer, yields $pO_2$ to the tissue. The electrode arrangement according to the invention can essentially assume three positions:

Position 1 in which a $pO_2$ value is measured very near the arterial value,

Position 2 the $pO_2$ value measured here lies between the arterial and the venous value and Position 3 the value measured here lies very near to venous $pO_2$-value.

The $pO_2$ value measured with the inventive electrode arrangement corresponds, if only on the basis of the previous theoretical explanation, always to a differential value between the arterial and the venous value. Since at the insertion of the electrode arrangement it is not known, which position an electrode arrangement or the measuring face will assume, the measured value will always indicate only a statement about the behavior of the $pO_2$ value in the tissue during a circulation alteration. This measurement is as test results have shown more important than the measurement of a $pO_2$ absolute value in the tissue itself. By measuring the differential value the actual oxygen supply of this tissue can be determined, wherein the skin is also representative for all inner organs. It has to be added that in case of circulation alterations for instance with lack of volume the final path of the current travel depicted in black in FIG. 6a changes the blood flow and thus the $pO_2$ transmittal to the tissue because of muscular changes of the wall. This means that the $pO_2$ measurement performed according to the invention is a criterium for the peripheral blood supply to the organ or blood supply to the skin as well as for its $pO_2$ supply.

The pO₂ drop during the performed measurement under labor in the upper segment of the FIG. 6a represents therefore the circulation dynamic share, while the second share indicates the genuine pO₂ regeneration phase. The drop of the pO₂ content between the arterial and the venous share of the tissue is illustrated in FIG. 6b.

Figure 6C:
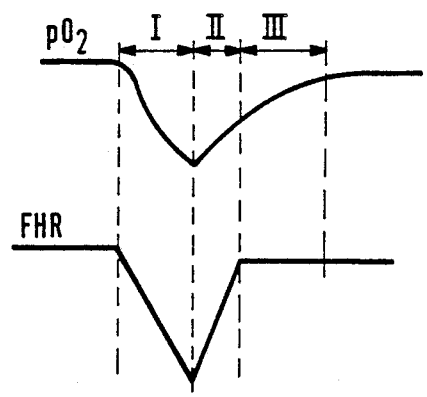
Figure 6B:
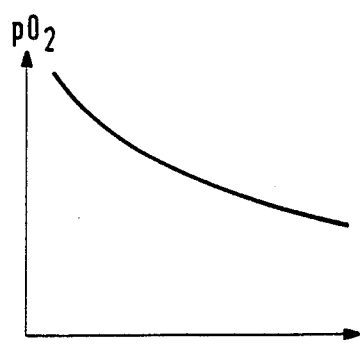

FIG. 6c shows in the upper region schematically the pO₂ sequence during a circulation dynamic depression phase of the child, for instance in case of the compression of the umbilical cord during a spasm. During such a depression phase I, the pO₂ in the tissue falls down to its lowest value. With the abatement of the umbilical cord compression a regeneration phase II begins, which transits into a tissue-pO₂-regeneration phase III, whose course essentially depends on how the umbilical cord compression is alleviated.

In the lower region of the FIG. 6c the course of the heart frequency pattern of the child is illustrated during the described phases I, II and III.

I claim:

1. A system for continuous pO₂ measurements in living, restlessly moving tissue, comprising an outer spiral metal tube electrode having a longitudinal wall, a spiral tubular plastic body arranged in the outer metal tube and an electrically insulated platinum wire electrode arranged in the spiral plastic body, and a cylindrical plastics body, wherein both metal electrodes (2, 14) are fit with one terminal end (6) in the cylindrical plastics body (26), the electrodes having a free end extending from the plastics body and having a ground-off front end face, the front end face and the longitudinal wall including an angle of about 20°, an insertion assistance means for inserting the electrodes into the tissue, the cylindrical plastics body being fastened in the insertion assistance means, the electrodes extending from the cylindrical plastics body, the system further comprising a pO₂ measuring apparatus, the platinum wire electrode being connected to the pO₂ measuring apparatus, and a second measuring apparatus, the metal tube electrode being connected to the second measuring apparatus, the two measuring apparatus having reference electrodes (54) independent of each other.

2. System according to claim 1, wherein the platinum wire electrode (2) is surrounded by a cellophane sleeve (7) within the metal tube electrode (14)

3. System according to claim 2, wherein the spiral tubular plastic body is of synthetic resin.

4. System according to claim 3, wherein the metal tube electrode (14) consists of V₂A-steel.

5. System according to one of the claims 1–4, wherein the plastics body (26) is a cylinder with a height (H) of approximately 5 mm and the diameter (D) of approximately 4.5 mm.

6. System according to claim 1, wherein the plastics body has a front face with an edge region, and wherein the metal tube electrode (14) is seated with the terminal end (6) of the platinum wire electrode (2) eccentrically in the edge region of the front face (29) of the plastics body (26).

7. System according to claim 1, wherein the platinum wire electrode (2) has a diameter (d) of approximately 20 μμm and is surrounded by a cellophane sleeve (7), and the cellophane sleeve (7) having an external diameter (a) of approximately 200 μm and an internal diameter (i) of approximately 180 μm.

8. System according to claim 1, wherein the metal tube electrode (14) has an external diameter (ad) of approximately 450 μm and an internal diameter (id) of approximately 300 μm.

9. System according to claim 1, wherein the metal tube electrode (14) with the platinum wire electrode (2) is a partial spiral winding with a slope (S) of approximately 30° 2nd with an external diameter (A), which is smaller than the diameter (D) of the plastics body (26).

10. System according to claim 1, wherein the free end of the platinum wire electrode defines a measuring face, and wherein the measuring face (4) of the platinum wire electrode (2) is offset backwards by a recess distance (5) behind the ground-off face (23).

11. System according to claim 10, wherein the recess distance (5) has a length (e) of less than 10 μm.

12. System according to claim 10, wherein the ground-off face (23) and the measuring face (4) are coated with an electrically insulating gas-permeable membrane (12).

13. System according to claim 12, wherein the membrane has a rearward portion (12a) which (12) fills out the recessed distance (5).

* * * * *